United States Patent [19]

Ni et al.

[11] Patent Number: 5,618,918
[45] Date of Patent: Apr. 8, 1997

[54] HUMAN BRAIN SODIUM DEPENDENT INORGANIC PHOSPHATE COTRANSPORTER

[75] Inventors: Binhui Ni; Steven M. Paul, both of Carmel, Ind.

[73] Assignee: Eli Lilly and Company, Indianapolis, Ind.

[21] Appl. No.: 647,481

[22] Filed: May 14, 1996

Related U.S. Application Data

[62] Division of Ser. No. 430,033, Apr. 27, 1995.

[51] Int. Cl.$^6$ ............... C07K 14/435; C07K 14/705
[52] U.S. Cl. ............................... 530/350; 530/300
[58] Field of Search ................... 530/300, 350; 536/23.1, 23.5; 435/7.1, 7.2, 69.1, 252.3, 240.1, 320.1

[56] References Cited

PUBLICATIONS

Ni et al. (1994) Soc. Neurosi. Abstr. 20: 825.
Collins et al. (1994) FASEB 8: 862–868.
Urade et al. (1991) PNAS 88: 1069–1073.
Masu et al. (1987) Nature 329: 836–838.
Chong et al. (1993) Genomics 18: 355–359.
Li et al. (1996) Cell Mol. Biol. Res. 5: 451–460.
Glinn et al. (1995) Soc. Neurosci. Abstr. 21: 2065.
Binhui Ni, et al., *Proc. Natl. Acad. Sci.*, vol. 91, pp. 5607–5611, Jun. 1994.

*Primary Examiner*—Stephen G. Walsh
*Assistant Examiner*—Kenneth A. Sorensen
*Attorney, Agent, or Firm*—Donna K. Blalock; David E. Boone

[57] ABSTRACT

This invention describes a novel human brain $Na^+$-dependent inorganic phosphate cotransporter, designated the hBNPI protein. This invention also encompasses nucleic acids encoding this protein, or a fragment thereof, as well as methods employing this protein and the nucleic acid compounds.

1 Claim, No Drawings

HUMAN BRAIN SODIUM DEPENDENT INORGANIC PHOSPHATE COTRANSPORTER

This application is a division of application Ser. No. 08/430,033 filed Apr. 27, 1995.

BACKGROUND OF THE INVENTION

Inorganic phosphate ($P_i$), a charged anion, is essential to bioenergetics, metabolic regulation, and bone and membrane structure. It is well known that $P_i$ homeostasis in the body depends primarily on mechanisms that govern the renal excretion of $P_i$ into the glomerular filtrate and its subsequent reabsorption against an electrochemical gradient via brush-border epithelial cells located in the proximal tubule of the kidney [J. Bonjour and J. Caverzasio, *Reviews in Physiological Pharmacology*, 100:161–214 (1985); V. W. Dennis, *Phosphate homeostasis*, in HANDBOOK OF PHYSIOLOGY, (S. Shultz, ed. 1991) at pages 1785–1815.] This transepithelial transport of $P_i$ is mediated, in part, by a transport system which is driven by the transmembrane $Na^+$ gradient across the microvilli brush border membrane. However, it remains largely unknown how cells transport and regulate necessary the intracellular concentrations of $P_i$, and the molecular events underlying this system. Experiments using isolated kidney tubules or brush-border membranes have shown that $P_i$ transport is rather complex, regulated not only by extracellular [$P_i$] but also by neurotransmitters such as catecholamines (for review see V. W. Dennis, supra), and by a variety of hormones and metabolic factors. Berndt and Knox, "Renal Regulation of Phosphate Excretion", in, THE KIDNEY. PHYSIOLOGY AND PATHOPHYSIOLOGY, (D. W. Seldin and G. Giebisch, eds., 1991) at pages 1381–1396. Renal denervation, for example, decreases sodium and phosphate reabsorption. Norepinephrine released from nerve endings in proximity to renal tubules acts on the proximal tubule to increase phosphate reabsorption. In studies of isolated tubules, however, dopamine is shown to inhibit phosphate and sodium transport in the rabbit proximal tubule. Furthermore, several studies also show than depletion of extracellular $P_i$ or increased circulating levels of parathyroid hormone alter the activity and expression of transporter molecules or both.

Several recent reports have demonstrated that $P_i$ homeostasis significantly affects the central nervous system (CNS). Phosphate/calcium alterations in serum, for example, have been implicated in the etiology and pathogenesis of Alzheimer's diseases. Depletion of high energy phosphates (phosphocreatine) and ATP is thought to be part of the final common pathway mediating excitotoxic neuronal cell death secondary to a wide variety of insults. Tight coupling between $P_i$ transport and ATP production has been observed in many cells and tissues. Chronic $P_i$ depletion in vivo is associated with a significant reduction in the ATP content of polymorphonuclear leukocytes, platelets, and various tissues including kidney, heart, and skeletal muscle. A similar observation has been made in cultured peripheral vagal nerves. This reduction in intracellular ATP has been shown to be a direct consequence of the decrease in intracellular $P_i$ which occurs following $P_i$ depletion. In addition to its possible role in ATP biosynthesis, several lines of evidence have suggested that $P_i$ may be involved in neuronal signalling events. In this regard, a study using brain tissue has recently shown that physiological concentrations of $P_i$ can enhance the ATP-dependent binding of $Ca^{++}$ to brain microsomes, resulting in a larger intracellular pool of $Ca^{++}$ releasable by inositol triphosphate. Our recent work have demonstrated that >90% $P_i$ transport in cortical neurons, which displays similar kinetic parameters to those reported for cultured kidney proximal tubule epithelial cells and membrane vesicles, are sodium dependent and that this $Na^+$-dependent transport system is regulated through a $Na^+$-dependent $P_i$ cotransporner. B. Ni, et al., *Proceedings of the National Academy of Sciences (USA)*, 91:5607–5611 (1994).

The present invention describes the cloning and characterization of a human brain $Na^+$-dependent $P_i$ cotransporter which is selectively expressed in discrete populations of neurons and glia. Fluorescent in situ hybridization (FISH) analysis demonstrates that this $Na^+$-dependent $P_i$ cotransporter is located in chromosome 19 (19q13.3) which has been linked to susceptible gene(s) for late onset Alzheimer's disease. M. Mullan and F. Crawford, *Trends in Neurological Sciences*, 16, 398–403 (1993). The characterization and treatment of physiological disorders is hereby furthered.

SUMMARY OF THE INVENTION

This invention provides an isolated amino acid compound useful as a human brain sodium-dependent inorganic phosphate cotransporter, said compound comprising the amino acid sequence Met Glu Phe Arg Gln Glu Glu Phe Arg Lys Leu Ala Gly Arg
1                 5                    10

Ala Leu Gly Lys Leu His Arg Leu Leu Glu Lys Arg Gln Glu
15                  20                  25

Gly Ala Glu Thr Leu Glu Leu Ser Ala Asp Gly Arg Pro Val
    30              35                  40

Thr Thr Gln Thr Arg Asp Pro Pro Val Val Asp Cys Thr Cys
        45              50                  55

Phe Gly Leu Pro Arg Arg Tyr Ile Ile Ala Ile Met Ser Gly
            60              65              70

Leu Gly Phe Cys Ile Ser Phe Gly Ile Arg Cys Asn Leu Gly
            75              80

Val Ala Ile Val Ser Met Val Asn Asn Ser Thr Thr His Arg
85              90                  95

Gly Gly His Val Val Val Gln Lys Ala Gln Phe Ser Trp Asp
    100             105                 110

Pro Glu Thr Val Gly Leu Ile His Gly Ser Phe Phe Trp Gly
        115             120                 125

Tyr Ile Val Thr Gln Ile Pro Gly Gly Phe Ile Cys Gln Lys
            130             135                 140

Phe Ala Ala Asn Arg Val Phe Gly Phe Ala Ile Val Ala Thr
                145                 150

Ser Thr Leu Asn Met Leu Ile Pro Ser Ala Ala Arg Val His
155                 160                 165

Tyr Gly Cys Val Ile Phe Val Arg Ile Leu Gln Gly Leu Val
    170             175                 180

Glu Gly Val Thr Tyr Pro Ala Cys His Gly Ile Trp Ser Lys
        185             190                 195

Trp Ala Pro Pro Leu Glu Arg Ser Arg Leu Ala Thr Thr Ala
            200             205                 210

Phe Cys Gly Ser Tyr Ala Gly Ala Val Val Ala Met Pro Leu
            215                 220

Ala Gly Val Leu Val Gln Tyr Ser Gly Trp Ser Ser Val Phe
225                 230             235

Tyr Val Tyr Gly Ser Phe Gly Ile Phe Trp Tyr Leu Phe Trp
    240             245                 250

| | | | | | | | | | | |
|---|---|---|---|---|---|---|---|---|---|---|
|Leu|Leu|Val|Ser|Tyr|Glu|Ser|Pro|Ala|Leu|His|Pro|Ser|Ile|
| | |255| | | |260| | | |265| |

Leu Leu Val Ser Tyr Glu Ser Pro Ala Leu His Pro Ser Ile
 255             260             265

Ser Glu Glu Glu Arg Lys Tyr Ile Glu Asp Ala Ile Gly Glu
         270             275             280

Ser Ala Lys Leu Met Asn Pro Leu Thr Lys Phe Ser Thr Pro
             285             290

Trp Arg Arg Phe Phe Thr Ser Met Pro Val Tyr Ala Ile Ile
295             300             305

Val Ala Asn Phe Cys Arg Ser Trp Thr Phe Tyr Leu Leu Leu
    310             315             320

Ile Ser Gln Pro Asp Tyr Phe Glu Glu Val Phe Gly Phe Glu
        325             330             335

Ile Ser Lys Val Gly Leu Val Ser Ala Leu Pro His Leu Val
            340             345             350

Met Thr Ile Ile Val Pro Ile Gly Gly Gln Ile Ala Asp Phe
                355             360

Leu Arg Ser Arg Arg Ile Met Ser Thr Thr Asn Val Arg Lys
365             370             375

Leu Met Asn Cys Gly Gly Phe Gly Met Glu Ala Thr Leu Leu
    380             385             390

Leu Val Val Gly Tyr Ser His Ser Lys Gly Val Ala Ile Ser
    395             400             405

Phe Leu Val Leu Ala Val Gly Phe Ser Gly Phe Ala Ile Ser
        410             415             420

Gly Phe Asn Val Asn His Leu Asp Ile Ala Pro Arg Tyr Ala
            425             430

Ser Ile Leu Met Gly Ile Ser Asn Gly Val Gly Thr Leu Ser
435             440             445

Gly Met Val Cys Pro Ile Ile Val Gly Ala Met Thr Lys His
    450             455             460

Lys Thr Arg Glu Glu Trp Gln Tyr Val Phe Leu Ile Ala Ser
        465             470             475

Leu Val His Tyr Gly Gly Val Ile Phe Tyr Gly Val Phe Ala
            480             485             490

Ser Gly Glu Lys Gln Pro Trp Ala Glu Pro Glu Glu Met Ser
                495             500

Glu Glu Lys Cys Gly Phe Val Gly His Asp Gln Leu Ala Gly
505             510             515

Ser Asp Asp Ser Glu Met Glu Asp Glu Ala Glu Pro Pro Gly
    520             525             530

Ala Pro Pro Ala Pro Pro Pro Ser Tyr Gly Ala Thr His Ser
        535             540             545

Thr Phe Gln Pro Pro Arg Pro Pro Pro Val Arg Asp Tyr
            550             555             560 hereinafter designated as SEQ ID NO:2.

The invention also provides an isolated nucleic acid compound that comprises a nucleic acid sequence which encodes for the amino acid compounds provided. Particularly this invention provides the isolated nucleic acid compound having the sequence

```
CGATAAGCTT GATATCGAAT TCCGGACTCT TGCTCGGGCG CCTTAACCCG GCGTTCGGTT    60

CATCCCGCAG CGCCAGTTCT GCTTACCAAA AGTGGCCCAC TAGGCACTCG CATTCCACGC   120

CCGGCTCCAC GCCAGCGAGC CGGGCTTCTT ACCCATTTAA AGTTTGAGAA TAGGTTGAGA   180

TCGTTTCGGC CCCAAGACCT CTAATCATTC GCTTTACCGG ATAAAACTGC GTGGCGGGGG   240

TGCGTCGGGT CTGCGAGAGC GCCAGCTATC CTGAGGGAAA CTTCGGAGGG AACCAGCTAC   300

TAGATGGTTC GATTAGTCTT TCGCCCCTAT ACCCAGGTCG ACGACCGAT TTGCACGTCA    360

GGACCGCTAC GGACCTCCAC CAGAGTTTCC TCTGGCTTCG CCCTGCCCAG GCGATCGGCG   420

GGGGGGACCC GCGGGGTGAC CGGCGGCAGG AGCCGCCACC ATG GAG TTC CGC CAG    475
                                              Met Glu Phe Arg Gln
                                               1               5

GAG GAG TTT CGG AAG CTA GCG GGT CGT GCT CTC GGG AAG CTG CAC CGC    523
            Glu Glu Phe Arg Lys Leu Ala Gly Arg Ala Leu Gly Lys Leu His Arg
                         10                  15                  20

CTT CTG GAG AAG CGG CAG GAA GGC GCG GAG ACG CTG GAG CTG AGT GCG    571
            Leu Leu Glu Lys Arg Gln Glu Gly Ala Glu Thr Leu Glu Leu Ser Ala
                     25                  30                  35

GAT GGG CGC CCG GTG ACC ACG CAG ACC CGG GAC CCG CCG GTG GTG GAC    619
            Asp Gly Arg Pro Val Thr Thr Gln Thr Arg Asp Pro Pro Val Val Asp
                     40                  45                  50

TGC ACC TGC TTC GGC CTC CCT CGC CGC TAC ATT ATC GCC ATC ATG AGT    667
            Cys Thr Cys Phe Gly Leu Pro Arg Arg Tyr Ile Ile Ala Ile Met Ser
                 55                  60                  65

GGT CTG GGC TTC TGC ATC AGC TTT GGC ATC CGC TGC AAC CTG GGC GTG    715
            Gly Leu Gly Phe Cys Ile Ser Phe Gly Ile Arg Cys Asn Leu Gly Val
             70                  75                  80                  85

GCC ATC GTC TCC ATG GTC AAT AAC AGC ACG ACC CAC CGC GGG GGC CAC    763
            Ala Ile Val Ser Met Val Asn Asn Ser Thr Thr His Arg Gly Gly His
                             90                  95                 100
```

```
GTG GTG GTG CAG AAA GCC CAG TTC AGC TGG GAT CCA GAG ACT GTC GGC        811
Val Val Val Gln Lys Ala Gln Phe Ser Trp Asp Pro Glu Thr Val Gly
            105                 110                 115

CTC ATA CAC GGC TCC TTT TTC TGG GGC TAC ATT GTC ACT CAG ATT CCA        859
Leu Ile His Gly Ser Phe Phe Trp Gly Tyr Ile Val Thr Gln Ile Pro
        120                 125                 130

GGA GGA TTT ATC TGT CAA AAA TTT GCA GCC AAC AGA GTT TTC GGC TTT        907
Gly Gly Phe Ile Cys Gln Lys Phe Ala Ala Asn Arg Val Phe Gly Phe
    135             140                 145

GCT ATT GTG GCA ACA TCC ACT CTA AAC ATG CTG ATC CCC TCA GCT GCC        955
Ala Ile Val Ala Thr Ser Thr Leu Asn Met Leu Ile Pro Ser Ala Ala
150             155                 160                 165

CGC GTC CAC TAT GGC TGT GTC ATC TTC GTG AGG ATC CTG CAG GGG TTG       1003
Arg Val His Tyr Gly Cys Val Ile Phe Val Arg Ile Leu Gln Gly Leu
            170                 175                 180

GTA GAG GGG GTC ACA TAC CCC GCC TGC CAT GGG ATC TGG AGC AAA TGG       1051
Val Glu Gly Val Thr Tyr Pro Ala Cys His Gly Ile Trp Ser Lys Trp
        185                 190                 195

GCC CCA CCC TTA GAA CGG AGT CGC CTG GCG ACG ACA GCC TTT TGT GGT       1099
Ala Pro Pro Leu Glu Arg Ser Arg Leu Ala Thr Thr Ala Phe Cys Gly
    200                 205                 210

TCC TAT GCT GGG GCG GTG GTC GCG ATG CCC CTC GCC GGG GTC CTT GTG       1147
Ser Tyr Ala Gly Ala Val Val Ala Met Pro Leu Ala Gly Val Leu Val
    215                 220                 225

CAG TAC TCA GGA TGG AGC TCT GTT TTC TAC GTC TAC GGC AGC TTC GGG       1195
Gln Tyr Ser Gly Trp Ser Ser Val Phe Tyr Val Tyr Gly Ser Phe Gly
230             235                 240                 245

ATC TTC TGG TAC CTG TTC TGG CTG CTC GTC TCC TAC GAG TCC CCC GCG       1243
Ile Phe Trp Tyr Leu Phe Trp Leu Leu Val Ser Tyr Glu Ser Pro Ala
            250                 255                 260

CTG CAC CCC AGC ATC TCG GAG GAG GAG CGC AAG TAC ATC GAG GAC GCC       1291
Leu His Pro Ser Ile Ser Glu Glu Glu Arg Lys Tyr Ile Glu Asp Ala
        265                 270                 275

ATC GGA GAG AGC GCG AAA CTC ATG AAC CCC CTC ACG AAG TTT AGC ACT       1339
Ile Gly Glu Ser Ala Lys Leu Met Asn Pro Leu Thr Lys Phe Ser Thr
    280                 285                 290

CCC TGG CGG CGC TTC TTC ACG TCT ATG CCA GTC TAT GCC ATC ATC GTG       1387
Pro Trp Arg Arg Phe Phe Thr Ser Met Pro Val Tyr Ala Ile Ile Val
    295                 300                 305

GCC AAC TTC TGC CGC AGC TGG ACG TTC TAC CTG CTC CTC ATC TCC CAG       1435
Ala Asn Phe Cys Arg Ser Trp Thr Phe Tyr Leu Leu Leu Ile Ser Gln
310             315                 320                 325

CCC GAC TAC TTC GAA GAA GTG TTC GGC TTC GAG ATC AGC AAG GTA GGC       1483
Pro Asp Tyr Phe Glu Glu Val Phe Gly Phe Glu Ile Ser Lys Val Gly
            330                 335                 340

CTG GTG TCC GCG CTG CCC CAC CTG GTC ATG ACC ATC ATC GTG CCC ATC       1531
Leu Val Ser Ala Leu Pro His Leu Val Met Thr Ile Ile Val Pro Ile
        345                 350                 355

GGC GGC CAG ATC GCG GAC TTC CTG CGG AGC CGC CGC ATC ATG TCC ACC       1579
Gly Gly Gln Ile Ala Asp Phe Leu Arg Ser Arg Arg Ile Met Ser Thr
    360                 365                 370

ACC AAC GTG CGC AAG TTG ATG AAC TGC GGA GGC TTC GGC ATG GAA GCC       1627
Thr Asn Val Arg Lys Leu Met Asn Cys Gly Gly Phe Gly Met Glu Ala
    375                 380                 385

ACG CTG CTG TTG GTG GTC GGC TAC TCG CAC TCC AAG GGC GTG GCC ATC       1675
Thr Leu Leu Leu Val Val Gly Tyr Ser His Ser Lys Gly Val Ala Ile
390             395                 400                 405

TCC TTC CTG GTC CTA GCC GTG GGC TTC AGC GGC TTC GCC ATC TCT GGG       1723
Ser Phe Leu Val Leu Ala Val Gly Phe Ser Gly Phe Ala Ile Ser Gly
            410                 415                 420

TTC AAC GTG AAC CAC CTG GAC ATA GCC CCG CGC TAC GCC AGC ATC CTC       1771
Phe Asn Val Asn His Leu Asp Ile Ala Pro Arg Tyr Ala Ser Ile Leu
        425                 430                 435
```

```
ATG GGC ATC TCC AAC GGC GTG GGC ACA CTG TCG GGC ATG GTG TGC CCC     1819
Met Gly Ile Ser Asn Gly Val Gly Thr Leu Ser Gly Met Val Cys Pro
        440                 445                 450

ATC ATC GTG GGG GCC ATG ACT AAG CAC AAG ACT CGG GAG GAG TGG CAG     1867
Ile Ile Val Gly Ala Met Thr Lys His Lys Thr Arg Glu Glu Trp Gln
    455                 460                 465

TAC GTG TTC CTA ATT GCC TCC CTG GTG CAC TAT GGA GGT GTC ATC TTC     1915
Tyr Val Phe Leu Ile Ala Ser Leu Val His Tyr Gly Gly Val Ile Phe
470                 475                 480                 485

TAC GGG GTC TTT GCT TCT GGA GAG AAG CAG CCG TGG GCA GAG CCT GAG     1963
Tyr Gly Val Phe Ala Ser Gly Glu Lys Gln Pro Trp Ala Glu Pro Glu
                490                 495                 500

GAG ATG AGC GAG GAG AAG TGT GGC TTC GTT GGC CAT GAC CAG CTG GCT     2011
Glu Met Ser Glu Glu Lys Cys Gly Phe Val Gly His Asp Gln Leu Ala
            505                 510                 515

GGC AGT GAC GAC AGC GAA ATG GAG GAT GAG GCT GAG CCC CCG GGG GCA     2059
Gly Ser Asp Asp Ser Glu Met Glu Asp Glu Ala Glu Pro Pro Gly Ala
        520                 525                 530

CCC CCT GCA CCC CCG CCC TCC TAT GGG GCC ACA CAC AGC ACA TTT CAG     2107
Pro Pro Ala Pro Pro Pro Ser Tyr Gly Ala Thr His Ser Thr Phe Gln
    535                 540                 545

CCC CCC AGG CCC CCA CCC CCT GTC CGG GAC TAC TGA CCATGTGCCT          2153
Pro Pro Arg Pro Pro Pro Pro Val Arg Asp Tyr  *
550                 555                 560

CCCACTGAAT GGCAGTTTCC AGGACCTCCA TTCCACTCAT CTCTGGCCTG AGTGACAGTG   2213

TCAAGGAACC CTGCTCCTCT CTGTCCTGCC TCAGGCCTAA GAAGCACTCT CCCTTGTTCC   2273

CAGTGCTGTC AAATCCTCTT TCCTTCCCAA TTGCCTCTCA GGGGTAGTGA AGCTGCAGAC   2333

TGACAGTTTC AAGGATACCC AAATTCCCCT AAAGGTTCCC TCTCCACCCG TTCTGCCTCA   2393

GTGGTTTCAA ATCTCTCCTT TCAGGGCTTT ATTTGAATGG ACAGTTCGAC CTCTTACTCT   2453

CTCTTGTGGT TTTGAGGCAC CCACACCCCC CGCTTTCCTT TATCTCCAGG GACTCTCAGG   2513

CTAACCTTTG AGATCACTCA GCTCCCATCT CCTTTCAGAA AAATTCAAGG TCCTCCTCTA   2573

GAAGTTTCAA ATCTCTCCCA ACTCTGTTCT GCATCTTCCA GATTGGTTTA ACCAATTACT   2633

CGTCCCCGCC ATTCCAGGGA TTGATTCTCA CCAGCGTTTC TGATGGAAAA TGGCGGGAAT   2693

TCCTGCAGCC CGGGGGATCC ACT                                          2716
``` which is hereinafter designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and adverse reaction profile of agents useful in the treatment or prevention of disorders associated with an inappropriate stimulation of a human brain Na$^+$-dependent inorganic phosphate cotransporter.

DETAILED DESCRIPTION AND PREFERRED EMBODIMENTS

The terms and abbreviations used in this document have their normal meanings unless otherwise designated. For example "C" refers to degrees Celsius; "N" refers to normal or normality; "mmol" refers to millimole or millimoles; "g" refers to gram or grams; "ml" means milliliter or milliliters; "M" refers to molar or molarity; "µg" refers to microgram or micrograms; and "µl" refers to microliter or microliters.

All nucleic acid sequences, unless otherwise designated, are written in the direction from the 5' end the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the are and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary.: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other brain $Na^+$-dependent inorganic phosphate cotransporter subtypes. This term may also be employed in the sense that such antibodies may be used to differentiate between the human hBNPI protein protein and analogous proteins derived from other species.

The term "PCR" as used herein refers to the widely-known polymerase chain reaction employing a thermally-stable polymerase.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, the entirety of which is herein incorporated by reference.

The principles of solid phase chemical synthesis of polypeptides are well known in the art and may be found in general texts in the area. See, e.g., H. Dugas and C. Penney, BIOORGANIC CHEMISTRY, (1981) at pages 54–92. For examples, peptides may be synthesized by solid-phase methodology utilizing an Applied Biosystems 430A peptide synthesizer (commercially available from Applied Biosystems, Foster City California) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% metacresol. Cleavage of the side chain protecting group(s) and of the peptide from the resin is carried out at zero degrees centigrade or below, preferably –20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector;

d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
| --- | --- |
| DH5α | F⁻ (φ80dlacZΔM15), Δ(lacZYA-argF)U169 supE44, λ⁻, hsdR17 ($r_K^-$, $m_K^+$), recA1, endA1, gyrA96, thi-1, relA1 |
| HB101 | supE44, hsdS20 ($r_B^-$ $m_B^-$), recA13, ara-14, proA2 lacY1, galK2, rpsL20, xyl-5, mtl-1, mcrB, mrr |
| JM109 | recA1, e14⁻(mcrA), supE44, endA1, hsdR17 ($r_K^-$, $m_K^+$), gyrA96, relA1, thi-1, Δ(lac-proAB), F'[traD36, proAB+ lacI$^q$, lacZΔM15] |
| RR1 | supE44, hsdS20 ($r_B^-$ $m_B^-$), ara-14 proA2, lacY1, galK2, rpsL20, xyl-5, mtl-5 |
| χ1776 | F⁻, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ- |
| 294 | endA, thi⁻, hsr⁻, hsm$_k^+$ (U.S. Pat. No. 4,366,246) |
| LE392 | F⁻, hsdR514 (r⁻m⁻), supE44, supF58, lacY1, or Δlac(I-Y)6, galK2, glaT22, metB1, trpR55, λ⁻ |

These strains are all commercially available from suppliers such as: Bethesda Research Laboratories, Gaithersburg, Md. 20877 and Stratagene Cloning Systems, La Jolla, Calif. 92037; or are readily available to the poblic from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial hose and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S. Pat. No. 4,551,433, issued Nov. 5, 1985.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature (London)*, 275:615 (1978); and Goeddel et al., *Nature (London)*, 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoners for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the nucleic acids of the present invention. Exemplary host cells suitable for use in the present invention are listed in Table I.

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA).*, 79:6777 (1982). The plasmid DMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, as well as co-pending U.S. patent application Ser. No. 07/368,700, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gone encoding the protein of interest. The skilled artisan understands that linkers or adapters may be employed in cloning the gone of interest into this BclI site. A depiction of the plasmid phd is provided as FIG. 2 of this document. The phd series of plasmids functions most efficiently when introduced into a host cell which produces the E1A gone product, cell lines such as AV12-664,293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., Supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YAp7 (ATCC-40053), for example, is commonly used. See, e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid DHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II, infra.

TABLE II

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the hBNPI protein molecule may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See, e.g., M. J. Gait, ed., OLIGONUCLEOTIDE SYNTHESIS, A PRACTICAL APPROACH, (1984).]

The synthetic human hBNPI protein gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the hBNPI protein. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence

| | | | | | |
|---|---|---|---|---|---|
| CGAUAAGCUU | GAUAUCGAAU | UCCGGACUCU | UGCUCGGGCG | CCUUAACCCG | GCGUUCGGUU | 60 |
| CAUCCCGCAG | CGCCAGUUCU | GCUUACCAAA | AGUGGCCCAC | UAGGCACUCG | CAUUCCACGC | 120 |
| CCGGCUCCAC | GCCAGCGAGC | CGGGCUUCUU | ACCCAUUUAA | AGUUUGAGAA | UAGGUUGAGA | 180 |
| UCGUUUCGGC | CCCAAGACCU | CUAAUCAUUC | GCUUUACCGG | AUAAAACUGC | GUGGCGGGGG | 240 |
| UGCGUCGGGU | CUGCGAGAGC | GCCAGCUAUC | CUGAGGGAAA | CUUCGGAGGG | AACCAGCUAC | 300 |
| UAGAUGGUUC | GAUUAGUCUU | UCGCCCCUAU | ACCCAGGUCG | GACGACCGAU | UUGCACGUCA | 360 |
| GGACCGCUAC | GGACCUCCAC | CAGAGUUUCC | UCUGGCUUCG | CCCUGCCCAG | GCGAUCGGCG | 420 |
| GGGGGGACCC | GCGGGGUGAC | CGGCGGCAGG | AGCCGCCACC | AUGGAGUUCC | GCCAGGAGGA | 480 |
| GUUUCGGAAG | CUAGCGGGUC | GUGCUCUCGG | GAAGCUGCAC | CGCCUUCUGG | AGAAGCGGCA | 540 |
| GGAAGGCGCG | GAGACGCUUG | AGCUGAGUGC | GGAUGGGCGC | CCGGUGACCA | CGCAGACCCG | 600 |
| GGACCCGCCG | GUGGUGGACU | GCACCUGCUU | CGGCCUCCCU | CGCCGCUACA | UUAUCGCCAU | 660 |
| CAUGAGUGGU | CUGGGCUUCU | GCAUCAGCUU | UGGCAUCCGC | UGCAACCUGG | GCGUGGCCAU | 720 |
| CGUCUCCAUG | GUCAAUAACA | GCACGACCCA | CCGCGGGGGC | CACGUGGUGG | UGCAGAAAGC | 780 |
| CCAGUUCAGC | UGGGAUCCAG | AGACUGUCGG | CCUCAUACAC | GGCUCCUUUU | UCUGGGGCUA | 840 |
| CAUUGUCACU | CAGAUUCCAG | GAGGAUUUAU | CUGUCAAAAA | UUUGCAGCCA | ACAGAGUUUU | 900 |
| CGGCUUUGCU | AUUGUGGCAA | CAUCCACUCU | AAACAUGCUG | AUCCCCUCAG | CUGCCCGCGU | 960 |
| CCACUAUGGC | UGUGUCAUCU | UCGUGAGGAU | CCUGCAGGGG | UUGGUAGAGG | GGGUCACAUA | 1020 |
| CCCCGCCUGC | CAUGGGAUCU | GGAGCAAAUG | GGCCCCACCC | UUAGAACGGA | GUCGCCUGGC | 1080 |
| GACGACAGCC | UUUUGUGGUU | CCAUGCUGG | GCGGUGGUC | GCGAUGCCCC | UCGCCGGGGU | 1140 |
| CCUUGUGCAG | UACUCAGGAU | GGAGCUCUGU | UUUCUACGUC | UACGGCAGCU | UCGGGAUCUU | 1200 |
| CUGGUACCUG | UUCUGGCUGC | UCGUCUCCUA | CGAGUCCCCC | GCGCUGCACC | CCAGCAUCUC | 1260 |
| GGAGGAGGAG | CGCAAGUACA | UCGAGGACGC | CAUCGGAGAG | AGCGCGAAAC | UCAUGAACCC | 1320 |
| CCUCACGAAG | UUUAGCACUUC | CCUGGCGGCG | CUUCUUCACG | UCUAUGCCAG | UCAUAUGCCAU | 1380 |
| CAUCGUGGCC | AACUUCUGCC | GCAGCUGGAC | GUUCUACCUG | CUGCUCAUCU | CCCAGCCCGA | 1440 |
| CUACUUCGAA | GAAGUGUUCG | GCUUCGAGAU | CAGCAAGGUA | GGCCUGGUGU | CCGCGCUGCC | 1500 |
| CCACCUGGUC | AUGACCAUCA | UCGUGCCCAU | CGGCGGCCAG | AUCGCGGACU | UCCUGCGGAG | 1560 |

| | | | | | |
|---|---|---|---|---|---|
| CCGCCGCAUC | AUGUCCACCA | CCAACGUGCG | CAAGUUGAUG | AACUGCGGAG | GCUUCGGCAU | 1620 |
| GGAAGCCACG | CUGCUGUUGG | UGGUCGGCUA | CUCGCACUCC | AAGGGCGUGG | CCAUCUCCUU | 1680 |
| CCUGGUCCUA | GCCGUGGGCU | UCAGCGGCUU | CGCCAUCUCU | GGGUUCAACG | UGAACCACCU | 1740 |
| GGACAUAGCC | CCGCGCUACG | CCAGCAUCCU | CAUGGGCAUC | UCCAACGGCG | UGGGCACACU | 1800 |
| GUCGGGCAUG | GUGUGCCCCA | UCAUCGUGGG | GGCCAUGACU | AAGCACAAGA | CUCGGGAGGA | 1860 |
| GUGGCAGUAC | GUGUUCCUAA | UUGCCUCCCU | GGUGCACUAU | GGAGGUGUCA | UCUUCUACGG | 1920 |
| GGUCUUUGCU | UCUGGAGAGA | AGCAGCCGUG | GGCAGAGCCU | GAGGAGAUGA | GCGAGGAGAA | 1980 |
| GUGUGGCUUC | GUUGGCCAUG | ACCAGCUGGC | UGGCAGUGAC | GACAGCGAAA | UGGAGGAUGA | 2040 |
| GGCUGAGCCC | CCGGGGGCAC | CCCCUGCACC | CCCGCCCUCC | UAUGGGGCCA | CACACAGCAC | 2100 |
| AUUUCAGCCC | CCCAGGCCCC | CACCCCCUGU | CCGGGACUAC | UGACCAUGUG | CCUCCCACUG | 2160 |
| AAUGGCAGUU | UCCAGGACCU | CCAUUCCACU | CAUCUCUGGC | CUGAGUGACA | GUGUCAAGGA | 2220 |
| ACCCUGCUCC | UCUCUGUCCU | GCCUCAGGCC | UAAGAAGCAC | UCUCCCUUGU | UCCCAGUGCU | 2280 |
| GUCAAAUCCU | CUUUCCUUCC | CAAUUGCCUC | UCAGGGGUAG | UGAAGCUGCA | GACUGACAGU | 2340 |
| UUCAAGGAUA | CCCAAAUUCC | CCUAAAGGUU | CCCUCUCCAC | CCGUUCUGCC | UCAGUGGUUU | 2400 |
| CAAAUCUCUC | CUUUCAGGGC | UUUAUUUGAA | UGGACAGUUC | GACCUCUUAC | UCUCUCUUGU | 2460 |
| GGUUUUGAGG | CACCCACACC | CCCCGCUUUC | CUUUAUCUCC | AGGGACUCUC | AGGCUAACCU | 2520 |
| UUGAGAUCAC | UCAGCUCCCA | UCUCCUUUCA | GAAAAAUUCA | AGGUCCUCCU | CUAGAAGUUU | 2580 |
| CAAAUCUCUC | CCAACUCUGU | UCUGCAUCUU | CCAGAUUGGU | UUAACCAAUU | ACUCGUCCCC | 2640 |
| GCCAUUCCAG | GGAUUGAUUC | UCACCAGCGU | UUCUGAUGGA | AAAUGGCGGG | AAUUCCUGCA | 2700 |
| GCCCGGGGGA | UCCACU | | | | | 2716 | hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template. complement thereof.

The most preferred systems for preparing the ribonucleic acids of the present invention employ the RNA polymerase from the bacteriophage T7 or the bacteriophage Sp6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to human genomic DNA or messenger RNA encoding a human brain $Na^+$-dependent inorganic phosphate cotransporter, is provided. Preferably, the 18 or more base pair compound is DNA.

The term "selectively hybridize" as used herein may refer to either of two situations. In the first such embodiment of this invention, the nucleic acid compounds described supra hybridize to a human sodium-dependent inorganic phosphate cotransporter under more stringent hybridization conditions than these same nucleic acid compounds would hybridize to an analogous sodium-dependent inorganic phosphate cotransporter of another species, e.g. murine or primate. In the second such embodiment of this invention, these probes hybridize to the hBNPI protein of the present invention under more stringent hybridization conditions than other related compounds, including nucleic acid sequences encoding other ion cotransporters.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA.

The sequence of SEQ ID NO:1 was prepared as follows: Molecular cloning of a human brain $Na^+$-dependent inorganic phosphate cotransporter(hBNPI)

Using a cDNA encoding the rat brain $Na^+$-dependent inorganic phosphate cotransporter (rBNPI)(Ni, et al., 1994), we screened, under low stringency conditions, a human cDNA library derived from hippocampus mRNAs. Twelve positive clones were isolated that strongly hybridized to the $^{32}$P-labeled probe rBNPI. Restriction endonuclease analysis and/or sequencing of these clones revealed two distinct sequences: those which are highly similar to the rBNPI (B. Ni, et al., 1994, supra) as well as the kidney $Na^+$-dependent inorganic phosphate cotransporter (Na/P$_i$), found in 10 clones, and those found in 2 clones which were proved to be rearrangments between the human putative phosphate transporter and other cDNAs. Of the 10 clones (designed as hBNP) which exhibited a strong similarity to rBNPI, 4 clones contained the 2.7 kb message. Sequence analysis of hBNPI predicts an open reading frame of 1683 bases, corresponding to a protein of 560 amino acids with an apparent molecular mass of 61,000 Da (61 kDa). The ATG initiation codon at position 1, which is preceded by an upstream, in-frame stop codon, matches the Kazak consensus initiation sequence for the initiation of translation.

Computer searching revealed that the protein encoded by the hBNPI shared significant sequence homology at the amino acid level with those of recently cloned rat rBNPI (98%), rabbit (31%) and human (31%) kidney phosphate transporter, $Na/P_i$, as indicated by comparison analysis. The highest degree of homology, which was found between rBNPI and hBNPI, suggested that hBNPI is the human homologue of the rat rBNPI. The segment of highest homology among the proteins is confined to a region that fits the proposed consensus $Na^+$-binding domain for various $Na^+$-dependent transporter systems (Deguchi et al., 1990). Alignment of the predicted hBNPI protein sequence with the consensus sequence indicated that amino acids leucine (L), glycine (G) and arginine (R) residues match the proposed motif and that other (F and R) are conservatively changed. The predicted hBNPI protein sequence also shares 41% and 32% amino acid identity with two proteins of unknown function from *Caenorhabditis elegans*, ZK512.6 and C38C10.2, respectively. J. Sulston et al., Nature (London), 356:37–41 (1992). A hydropathy plot of the deduced amino acid sequence of hBNPI suggests the presence of at least 6 to 8 transmembrane regions. This number of membrane-spanning domains is a characteristic structural motif of transport proteins. Based on the convention that activity of neuronal $P_i$ transport correlates with ATP synthesis and intracellular energy charge, we have modelled hBNPI protein secondary structure with 6 transmembrane domains, which is consistent with those of other energy-linked anion transporters. The putative two glycosylation sites and two protein kinase C phosphorylation sites and four putative calmodulin-dependent kinase II phosphorylation sites are well conserved.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

when preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The starting plasmids employed to prepare the vectors of the present invention may be isolated from the appropriate *E. coli* containing these plasmids using standard procedures such as cesium chloride DNA isolation.

The plasmids of the present invention may be readily modified to construct expression vectors that produce hBNPI proteins in a variety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, CURRENT PROTOCOLS IN MOLECULAR BIOLOGY, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is *E. coli*. An especially preferred expression vector in *E. coli* is one which comprises SEQ ID NO:1. Transformed host cells may be cultured under conditions well known to skilled artisans such that SEQ ID NO:2 is expressed, thereby producing Yb in the recombinant host cell.

The ability of ions to bind to the hBNPI protein is essential in the development of a multitude of indications. In developing agents which act as antagonists or agonists of the hBNPI protein, it would be desirable, therefore, to determine those agents which bind the hBNPI protein. Generally, such an assay includes a method for determining whether a substance is a functional ligand of the hBNPI protein, said method comprising contacting a functional compound of the hBNPI protein with said substance, monitoring binding activity by physically detectable means, and identifying those substances which effect a chosen response. Preferably, the physically detectable means is competition with labeled inorganic phosphate or binding of ligand in an oocyte transient expression system The instant invention provides such a screening system useful for discovering agents which compete with inorganic phosphate for binding to the hBNPI protein, said screening system comprising the steps of:

a) isolating a human hBNPI protein;

b) exposing said human hBNPI protein to a potential inhibitor or surrogate of the $P_i$/hBNPI protein complex;

c) introducing $P_i$;

d) removing non-specifically bound molecules; and e) quantifying the concentration of bound potential inhibitor and/or $P_i$.

This allows one to rapidly screen for inhibitors or surrogates of the formation of the $P_i$/hBNPI protein complex. Utilization of the screening system described above provides a sensitive and rapid means to determine compounds which interfere with the formation of the $P_i$/hBNPI protein complex. This screening system may also be adapted to automated procedures such as a PANDEX® (Baxter-Dade Diagnostics) system allowing for efficient high-volume screening of potential therapeutic agents.

In such a screening protocol a hBNPI protein is prepared as elsewhere described herein, preferably using recombinant DNA technology. A sample of a test compound is then introduced to the reaction vessel containing the hBNPI protein followed by the addition of $P_i$. In the alternative the $P_i$ may be added simultaneously with the test compound. Unbound molecules are washed free and the eluent inspected for the presence of $P_i$ or the test compound.

For example, in a preferred method of the invention, radioactively labeled $P_i$ may be used. The eluent is then scored for the radioactivity. The absence or diminution of the chemical label or radioactivity indicates the formation of the $P_i$/hBNPI protein complex. This indicates that the test compound has not effectively competed with $P_i$ in the formation of the $P_i$/hBNPI protein complex. The presence of the chemical label or radioactivity indicates that the test compound has competed with $P_i$ in the formation of the $P_i$/hBNPI protein complex. Similarly, a radioactively or chemically labeled test compound may be used in which case the same steps as outlined above would be used except that the interpretation of results would be the converse of using radioactively labelled $P_i$.

As would be understood by the skilled artisan these assays may also be performed such that the practitioner measures the radioactivity remaining with the protein, not in the eluent. A preferred such assay employs radiolabeled $P_i$. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The hBNPI protein may be free in solution or bound to a solid support. Whether the hBNPI protein is bound to a support or is free in solution, it is generally important that the conformation of the protein be conserved. In a preferred practice of the invention, therefore, the hBNPI protein is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to hBNPI protein, because skilled artisans will recognize that any information regarding binding or selectivity of a particular compound is beneficial in the pharmaceutical development of drugs.

Assays useful for evaluating ion channel cotransporters are well known in the art. See, e.g., B. Ni, et al., supra. One such assay is described below.

Functional analysis of hBNPI in transfected COS-1 cells

To confirm the functional properties of the hBNPI protein, we constructed the hBNPI cDNA into a mammalian expression vector (pcDNA3) and transfected the pcDNA3-hBNPI constructs into the COS-1 cells. Sodium-dependent $^{32}$Pi uptake in the cells transfected with hBNPI was stimulated 2–3 fold above that of those transfected with vectors alone or of nontransfected cells. Replacement of sodium chloride with choline chloride reduced $^{32}$Pi uptake to background levels. Northern blot analysis was employed to examine the expression of hBNPI gene in transfected COS-1 cell lines. Labeled hBNPI cDNA detected strong expression of hBNPI transcripts in the COS-1 cells transfected with hBNPI but not in those cells transfected with the vector alone.

Expression of hBNPI mRNA in human brain

We examined hBNPI expression in multiple human tissues by probing polyadenylated RNA from heart, brain, placenta, lung, liver, skeletal muscle, kidney, pancreas, spleen, thymus, prostate, testis, ovary, small intestine, colon and peripheral blood leukocytes. The Northern blot analysis demonstrated that hBNPI probe detected a single mRNA species of 2.8 kb and strong expression of hBNPI transcript in the brain tissue. Trace levels of the hBNPI could be detected in RNA fractions from the small intestine, colon and testis if the blot was overexposured for a longer period of time (five days versus the usual one day exposure). No signal could be detected in the other tissues. The level of hBNPI in the brain fraction is at least 100 times higher than that in the intestine or colon. Northern blot analysis with multiple human brain regions shows that hBNPI mRNA is expressed in specific brain regions: most abundantly in neuron-enriched areas such as the amygdala and hippocampus; at moderate levels in glia-enriched areas such as the corpus callosum; and at low levels in the substantia niga, subthalamic nuclei and thalamus. No hBNPI transcript was detected in RNAs isolated from the caudate nucleus and hypothalamus.

A Northern blot of human brain mRNA isolated from fetal and adult (37 yr-old) brain was prepared for the characterization of expression of the hBNPI during brain development. The blot was hybridized with $^{32}$P-labeled hBNPI cDNA and human β-actin cDNA. The relative abundance of hBNPI mRNA shows a dramatic increase during postnatal development.

In situ hybridization histochemistry was employed to examine cells which express hBNPI transcripts in the human brain. hBNPI mRNA is highly expressed in the hippocampus formation and cerebral cortex. While the hybridization signal is present in various layers of the cerebral cortex, it appears to be more abundant in the neuronal layer v-vi where a distinct labeling is observed of pyramidal and non-pyramidal neurons. On closer inspection, it is apparent that hBNPI transcripts are concentrated in the pyramidal neurons of hippocampus and granule neurons of dentate gyrus. The hybridization signal was also detected in gila-enriched areas such as the corpus callosum, a finding which is consistent with data observed in Northern blot analysis of hBNPI mRNA in the human brain, and which suggests that, unlike its rat counterpart rBNPI, the hBNPI mRNA is expressed not only in neurons but also in glia as well. Cf., Ni, et al., supra.

Genomic analysis of the hBNPI gene

Genomic Southern blotting is a valuable tool for identifying homologous genes in various species. We used hBNPI cDNA to detect hBNPI genes in a variety of vertebrate species under stringent hybridization condition. The species tested included human, monkey, rat, mouse, dog, cow, rabbit, chicken and yeast. One major fragment which appears to harbor hBNPI gene was detected in the human, monkey, dog, cow and rabbit. Two fragments generated by internal EcoRI sites were detected in the rat and mouse. No signal was detected in yeast DNA. The results suggest that hBNPI sequence is well conserved among vertebrate species.

Genomic DNAs derived from four human individuals were digested with restriction endonucleases and used to determine the hBNPI gene structure and possible polymorphisms by Southern blot techniqus utilizing the full length hBNPI cDNA as a probe. The restriction patterns derived from 9 restrictions endonuclases are rather simple, and are similar between the four individuals. One major hybridizing fragment is generated by internal EcoRI, BglII, HindII, PstI, PvuII, respectively. One major fragment with multiple weak hybridizing bands was generated by internal digestion with TaqI, MpsI and BamHI. The results suggest that hBNPI gene structure is compact, that it is most likely present as a single copy, and that no polymorphisms of hBNPI gene exist.

Chromosome localization

Using hBNPI cDNA we screened a library constructed with human leukocyte DNA to isolate the hBNPI gene. After several rounds of screening, a 23 kb DNA fragment was isolated and identified as hBNPI gene. The hBNPI gene was labeled with digoxigenin dUTP by nick translation and hybridized to normal metaphase chromosomes derived from PHA-stimulated peripheral blood lymphocytes using a fluorescent in situ hybridization (FISH) technique. A specific hybridization signal was detected in the long arm of chromosome 19. Assignment of the hBNPI gene to the region of 19 was further confirmed by colocalization of a chromosome 19 specific probe, E2A, with the hBNPI gene. Measurements of ten specifically hybridized chromosomes 19 demonstrated that hBNPI gene is located 66% of the distance from the centromere to the telomere of chromosome arm 19q, an area that corresponds to band 19q13.3. No positive signals were observed in any other chromosomes. Analysis of interphase cells show only one copy of the probe present in the human genome, a finding which is consistent with the results of the genomic Southern blot.

The previously described screening systems identify compounds which competitively bind to the hBNPI protein. Determination of the ability of such compounds to stimulate or inhibit the action of the hBNPI protein is essential to further development of such compounds for therapeutic applications. The need for a bioactivity assay system which determines the response of the hBNPI protein to a compound is clear. The instant invention provides such a bioactivity assay, said assay comprising the steps of:

a) transfecting a mammalian host cell with an expression vector comprising DNA encoding a hBNPI protein;

b) culturing said host cell under conditions such that the DNA encoding the hBNPI protein is expressed, c) exposing said host cell so transfected to a test compound, and d) measuring the change in a physiological condition known to be influenced by the binding of a cation to the hBNPI protein relative to a control in which the transfected host cell is not exposed to the test compound.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of radiolabeled phosphate uptake was performed. The inhibition of phosphate uptake is a relatively simple assay used to determine thsoe agents which negatively affect the proteins of the present invention.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See e.g., C. Milstein, HANDBOOK OF EXPERIMENTAL IMMUNOLOGY, (Blackwell Scientific Pub., 1986); J. Goding, Monoclonal ANTIBODIES: PRINCIPLES AND PRACTICE, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued March 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., Science 242:423–426 (1988); Patent Cooperation Treaty Publication No. WO 88/01649, which was published 10 Mar. 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of hBNPI proteins.

In addition to being functional as direct therapeutic and diagnostic aids, the availability of a family of antibodies which are specific for the hBNPI protein enables the development of numerous assay systems for detecting agents which bind to this protein. One such assay system comprises radiolabeling hBNPI protein-specific antibodies with a radionuclide such as 125I and measuring displacement of the radiolabeled hBNPI protein-specific antibody from solid phase hBNPI protein in the presence of a potential antagonist or inhibitor.

Numerous other assay systems are also readily adaptable to detect agents which bind hBNPI protein. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the hBNPI protein, this invention also provides antibodies which are specific for the hypervariable regions of the anti-hBNPI protein antibodies. Some such anti-idiotypic antibodies would resemble the original epitope, the hBNPI protein, and, therefore, would be useful in evaluating the effectiveness of compounds which are potential antagonists, agonists, or partial agonists of the hBNPI protein. See, e.g., Cleveland, et al., *Nature (London)*, 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-hBNPI protein antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

We claim:

1. An isolated human brain Na$^+$-dependent inorganic phosphate cotransporter which comprises the amino acid sequence Met Glu Phe Arg Gln Glu Glu Phe Arg Lys Leu Ala Gly Arg
1                    5                        10

Ala Leu Gly Lys Leu His Arg Leu Leu Glu Lys Arg Gln Glu
15                   20                       25

Gly Ala Glu Thr Leu Glu Leu Ser Ala Asp Gly Arg Pro Val
         30                  35                      40

Thr Thr Gln Thr Arg Asp Pro Pro Val Val Asp Cys Thr Cys
             45                  50                  55

Phe Gly Leu Pro Arg Arg Tyr Ile Ile Ala Ile Met Ser Gly
             60                  65                  70

Leu Gly Phe Cys Ile Ser Phe Gly Ile Arg Cys Asn Leu Gly
                75                  80

Val Ala Ile Val Ser Met Val Asn Asn Ser Thr Thr His Arg
85                   90                       95

Gly Gly His Val Val Val Gln Lys Ala Gln Phe Ser Trp Asp
     100                 105                     110

Pro Glu Thr Val Gly Leu Ile His Gly Ser Phe Phe Trp Gly
         115                 120                     125

Tyr Ile Val Thr Gln Ile Pro Gly Gly Phe Ile Cys Gln Lys
             130                 135                 140

Phe Ala Ala Asn Arg Val Phe Gly Phe Ala Ile Val Ala Thr
                 145                     150

Ser Thr Leu Asn Met Leu Ile Pro Ser Ala Ala Arg Val His
155                  160                     165

Tyr Gly Cys Val Ile Phe Val Arg Ile Leu Gln Gly Leu Val
     170                 175                     180

Glu Gly Val Thr Tyr Pro Ala Cys His Gly Ile Trp Ser Lys
         185                 190                     195

Trp Ala Pro Pro Leu Glu Arg Ser Arg Leu Ala Thr Thr Ala
             200                 205                 210

Phe Cys Gly Ser Tyr Ala Gly Ala Val Val Ala Met Pro Leu
             215                     220

Ala Gly Val Leu Val Gln Tyr Ser Gly Trp Ser Ser Val Phe
225                  230                     235

Tyr Val Tyr Gly Ser Phe Gly Ile Phe Trp Tyr Leu Phe Trp
240                      245                     250

Leu Leu Val Ser Tyr Glu Ser Pro Ala Leu His Pro Ser Ile
             255                 260                 265

Ser Glu Glu Arg Lys Tyr Ile Glu Asp Ala Ile Gly Glu
         270                 275                     280

Ser Ala Lys Leu Met Asn Pro Leu Thr Lys Phe Ser Thr Pro
                 285                     290

Trp Arg Arg Phe Phe Thr Ser Met Pro Val Tyr Ala Ile Ile
295                  300                     305

Val Ala Asn Phe Cys Arg Ser Trp Thr Phe Tyr Leu Leu Leu
     310                 315                     320

Ile Ser Gln Pro Asp Tyr Phe Glu Glu Val Phe Gly Phe Glu
         325                 330                     335

Ile Ser Lys Val Gly Leu Val Ser Ala Leu Pro His Leu Val
             340                 345                 350

Met Thr Ile Ile Val Pro Ile Gly Gly Gln Ile Ala Asp Phe
                 355                     360

Leu Arg Ser Arg Arg Ile Met Ser Thr Thr Asn Val Arg Lys
365                      370                     375

Leu Met Asn Cys Gly Gly Phe Gly Met Glu Ala Thr Leu Leu
         380                     385                 390

Leu Val Val Gly Tyr Ser His Ser Lys Gly Val Ala Ile Ser
     395                     400                 405

Phe Leu Val Leu Ala Val Gly Phe Ser Gly Phe Ala Ile Ser
             410                     415             420

Gly Phe Asn Val Asn His Leu Asp Ile Ala Pro Arg Tyr Ala
                 425                     430

Ser Ile Leu Met Gly Ile Ser Asn Gly Val Gly Thr Leu Ser
435                      440                     445

Gly Met Val Cys Pro Ile Ile Val Gly Ala Met Thr Lys His
     450                     455                 460

Lys Thr Arg Glu Glu Trp Gln Tyr Val Phe Leu Ile Ala Ser
         465                     470                 475

Leu Val His Tyr Gly Gly Val Ile Phe Tyr Gly Val Phe Ala
             480                     485             490

Ser Gly Glu Lys Gln Pro Trp Ala Glu Pro Glu Glu Met Ser
                     495                     500

| Glu | Glu | Lys | Cys | Gly | Phe | Val | Gly | His | Asp | Gln | Leu | Ala | Gly |
| 505 | | | | | 510 | | | | | 515 | | | |

| Ser | Asp | Asp | Ser | Glu | Met | Glu | Asp | Glu | Ala | Glu | Pro | Pro | Gly |
| | 520 | | | | | 525 | | | | | 530 | | |

| Ala | Pro | Pro | Ala | Pro | Pro | Pro | Ser | Tyr | Gly | Ala | Thr | His | Ser |
| | 535 | | | | | | 540 | | | | | 545 | |

| Thr | Phe | Gln | Pro | Pro | Arg | Pro | Pro | Pro | Val | Arg | Asp | Tyr |
| | | | 550 | | | | 555 | | | | | 560 | which is SEQ ID NO:2, or a fragment of at least 6 continuous amino acids thereof.

* * * * *

UNITED STATES PATENT AND TRADEMARK OFFICE
CERTIFICATE OF CORRECTION

PATENT NO. : 5,618,918
DATED : April 8, 1997
INVENTOR(S) : Binhui Ni, et al.

Page 1 of 2

It is certified that error appears in the above-identified patent and that said Letters Patent is hereby corrected as shown below:

Column 2, line 7, delete "cotransporner" and insert therefore --cotransporter--.

Column 9, line 17, delete "are" and insert therefore --art--.

Column 12, line 40, delete "hose" and insert therefore --host--.

Column 13, line 2, delete "Promoners" and insert therefore --Promoters--.

Column 14, line 46, delete "DMSVi" and insert therefore --PMSVi--.

Column 15, lines 13-19, delete "gone" and insert therefore --gene--.

Column 15, line 55, delete " DHcGAPC1" and insert therefore --PHcGAPC1--.

Column 17, line 600, delete "GAGACGCUUG" and insert therefore --GAGACGCUGG--.

Column 17, line 1140, delete "CCAUGCUGG" and insert therefore --CCUAUGCUGG--.

Column 17, line 1380, delete "UUUAGCACUUC" and insert therefore --UUUAGCACUC--.

UNITED STATES PATENT AND TRADEMARK OFFICE
CERTIFICATE OF CORRECTION

PATENT NO. : 5,618,918
DATED : April 8, 1997
INVENTOR(S) : Binhui Ni, et al.

It is certified that error appears in the above-identified patent and that said Letters Patent is hereby corrected as shown below:

Column 18, line 1380, delete "UCAUAUGCCAU" and insert therefore --UCUAUGCCAU--.

Column 25, line 24, delete "gila" and insert therefore --glia--.

Column 27, line 40, delete "Leachings" and insert therefore --Teaching--.

Signed and Sealed this

Eighth Day of September, 1998

Attest:

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2716 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 461..2140

( x i ) SEQUENCE DESCRIPTION: SEQ ID NO:1:

```
CGATAAGCTT  GATATCGAAT  TCCGGACTCT  TGCTCGGGCG  CCTTAACCCG  GCGTTCGGTT          60

CATCCCGCAG  CGCCAGTTCT  GCTTACCAAA  AGTGGCCCAC  TAGGCACTCG  CATTCCACGC         120

CCGGCTCCAC  GCCAGCGAGC  CGGGCTTCTT  ACCCATTTAA  AGTTTGAGAA  TAGGTTGAGA         180

TCGTTTCGGC  CCCAAGACCT  CTAATCATTC  GCTTTACCGG  ATAAAACTGC  GTGGCGGGGG         240

TGCGTCGGGT  CTGCGAGAGC  GCCAGCTATC  CTGAGGGAAA  CTTCGGAGGG  AACCAGCTAC         300

TAGATGGTTC  GATTAGTCTT  TCGCCCCTAT  ACCCAGGTCG  GACGACCGAT  TTGCACGTCA         360

GGACCGCTAC  GGACCTCCAC  CAGAGTTTCC  TCTGGCTTCG  CCCTGCCCAG  GCGATCGGCG         420

GGGGGACCC  GCGGGGTGAC  CGGCGGCAGG  AGCCGCCACC  ATG GAG TTC CGC CAG           475
                                                Met Glu Phe Arg Gln
                                                 1               5

GAG GAG TTT CGG AAG CTA GCG GGT CGT GCT CTC GGG AAG CTG CAC CGC              523
Glu Glu Phe Arg Lys Leu Ala Gly Arg Ala Leu Gly Lys Leu His Arg
             10                  15                  20

CTT CTG GAG AAG CGG CAG GAA GGC GCG GAG ACG CTG GAG CTG AGT GCG              571
Leu Leu Glu Lys Arg Gln Glu Gly Ala Glu Thr Leu Glu Leu Ser Ala
         25                  30                  35

GAT GGG CGC CCG GTG ACC ACG CAG ACC CGG GAC CCG CCG GTG GTG GAC              619
Asp Gly Arg Pro Val Thr Thr Gln Thr Arg Asp Pro Pro Val Val Asp
     40                  45                  50

TGC ACC TGC TTC GGC CTC CCT CGC CGC TAC ATT ATC GCC ATC ATG AGT              667
Cys Thr Cys Phe Gly Leu Pro Arg Arg Tyr Ile Ile Ala Ile Met Ser
 55                  60                  65

GGT CTG GGC TTC TGC ATC AGC TTT GGC ATC CGC TGC AAC CTG GGC GTG              715
Gly Leu Gly Phe Cys Ile Ser Phe Gly Ile Arg Cys Asn Leu Gly Val
 70                  75                  80                  85

GCC ATC GTC TCC ATG GTC AAT AAC AGC ACG ACC CAC CGC GGG GGC CAC              763
Ala Ile Val Ser Met Val Asn Asn Ser Thr Thr His Arg Gly Gly His
                 90                  95                 100

GTG GTG GTG CAG AAA GCC CAG TTC AGC TGG GAT CCA GAG ACT GTC GGC              811
Val Val Val Gln Lys Ala Gln Phe Ser Trp Asp Pro Glu Thr Val Gly
            105                 110                 115

CTC ATA CAC GGC TCC TTT TTC TGG GGC TAC ATT GTC ACT CAG ATT CCA              859
Leu Ile His Gly Ser Phe Phe Trp Gly Tyr Ile Val Thr Gln Ile Pro
        120                 125                 130

GGA GGA TTT ATC TGT CAA AAA TTT GCA GCC AAC AGA GTT TTC GGC TTT              907
Gly Gly Phe Ile Cys Gln Lys Phe Ala Ala Asn Arg Val Phe Gly Phe
    135                 140                 145

GCT ATT GTG GCA ACA TCC ACT CTA AAC ATG CTG ATC CCC TCA GCT GCC              955
Ala Ile Val Ala Thr Ser Thr Leu Asn Met Leu Ile Pro Ser Ala Ala
```

-continued

| | | | | | | | | | | | | | | | | |
|---|---|---|---|---|---|---|---|---|---|---|---|---|---|---|---|---|
| 150 | | | | | 155 | | | | | 160 | | | | | 165 | |

| CGC | GTC | CAC | TAT | GGC | TGT | GTC | ATC | TTC | GTG | AGG | ATC | CTG | CAG | GGG | TTG | 1003 |
| Arg | Val | His | Tyr | Gly | Cys | Val | Ile | Phe | Val | Arg | Ile | Leu | Gln | Gly | Leu | |
| | | | | 170 | | | | 175 | | | | | 180 | | | |

| GTA | GAG | GGG | GTC | ACA | TAC | CCC | GCC | TGC | CAT | GGG | ATC | TGG | AGC | AAA | TGG | 1051 |
| Val | Glu | Gly | Val | Thr | Tyr | Pro | Ala | Cys | His | Gly | Ile | Trp | Ser | Lys | Trp | |
| | | | 185 | | | | | 190 | | | | | 195 | | | |

| GCC | CCA | CCC | TTA | GAA | CGG | AGT | CGC | CTG | GCG | ACG | ACA | GCC | TTT | TGT | GGT | 1099 |
| Ala | Pro | Pro | Leu | Glu | Arg | Ser | Arg | Leu | Ala | Thr | Thr | Ala | Phe | Cys | Gly | |
| | | 200 | | | | | 205 | | | | | 210 | | | | |

| TCC | TAT | GCT | GGG | GCG | GTG | GTC | GCG | ATG | CCC | CTC | GCC | GGG | GTC | CTT | GTG | 1147 |
| Ser | Tyr | Ala | Gly | Ala | Val | Val | Ala | Met | Pro | Leu | Ala | Gly | Val | Leu | Val | |
| | 215 | | | | | 220 | | | | | 225 | | | | | |

| CAG | TAC | TCA | GGA | TGG | AGC | TCT | GTT | TTC | TAC | GTC | TAC | GGC | AGC | TTC | GGG | 1195 |
| Gln | Tyr | Ser | Gly | Trp | Ser | Ser | Val | Phe | Tyr | Val | Tyr | Gly | Ser | Phe | Gly | |
| 230 | | | | | 235 | | | | | 240 | | | | | 245 | |

| ATC | TTC | TGG | TAC | CTG | TTC | TGG | CTG | CTC | GTC | TCC | TAC | GAG | TCC | CCC | GCG | 1243 |
| Ile | Phe | Trp | Tyr | Leu | Phe | Trp | Leu | Leu | Val | Ser | Tyr | Glu | Ser | Pro | Ala | |
| | | | | 250 | | | | | 255 | | | | | 260 | | |

| CTG | CAC | CCC | AGC | ATC | TCG | GAG | GAG | GAG | CGC | AAG | TAC | ATC | GAG | GAC | GCC | 1291 |
| Leu | His | Pro | Ser | Ile | Ser | Glu | Glu | Glu | Arg | Lys | Tyr | Ile | Glu | Asp | Ala | |
| | | | 265 | | | | | 270 | | | | | 275 | | | |

| ATC | GGA | GAG | AGC | GCG | AAA | CTC | ATG | AAC | CCC | CTC | ACG | AAG | TTT | AGC | ACT | 1339 |
| Ile | Gly | Glu | Ser | Ala | Lys | Leu | Met | Asn | Pro | Leu | Thr | Lys | Phe | Ser | Thr | |
| | | 280 | | | | | 285 | | | | | 290 | | | | |

| CCC | TGG | CGG | CGC | TTC | TTC | ACG | TCT | ATG | CCA | GTC | TAT | GCC | ATC | ATC | GTG | 1387 |
| Pro | Trp | Arg | Arg | Phe | Phe | Thr | Ser | Met | Pro | Val | Tyr | Ala | Ile | Ile | Val | |
| | 295 | | | | | 300 | | | | | 305 | | | | | |

| GCC | AAC | TTC | TGC | CGC | AGC | TGG | ACG | TTC | TAC | CTG | CTC | CTC | ATC | TCC | CAG | 1435 |
| Ala | Asn | Phe | Cys | Arg | Ser | Trp | Thr | Phe | Tyr | Leu | Leu | Leu | Ile | Ser | Gln | |
| 310 | | | | | 315 | | | | | 320 | | | | | 325 | |

| CCC | GAC | TAC | TTC | GAA | GAA | GTG | TTC | GGC | TTC | GAG | ATC | AGC | AAG | GTA | GGC | 1483 |
| Pro | Asp | Tyr | Phe | Glu | Glu | Val | Phe | Gly | Phe | Glu | Ile | Ser | Lys | Val | Gly | |
| | | | | 330 | | | | | 335 | | | | | 340 | | |

| CTG | GTG | TCC | GCG | CTG | CCC | CAC | CTG | GTC | ATG | ACC | ATC | ATC | GTG | CCC | ATC | 1531 |
| Leu | Val | Ser | Ala | Leu | Pro | His | Leu | Val | Met | Thr | Ile | Ile | Val | Pro | Ile | |
| | | | 345 | | | | | 350 | | | | | 355 | | | |

| GGC | GGC | CAG | ATC | GCG | GAC | TTC | CTG | CGG | AGC | CGC | CGC | ATC | ATG | TCC | ACC | 1579 |
| Gly | Gly | Gln | Ile | Ala | Asp | Phe | Leu | Arg | Ser | Arg | Arg | Ile | Met | Ser | Thr | |
| | | 360 | | | | | 365 | | | | | 370 | | | | |

| ACC | AAC | GTG | CGC | AAG | TTG | ATG | AAC | TGC | GGA | GGC | TTC | GGC | ATG | GAA | GCC | 1627 |
| Thr | Asn | Val | Arg | Lys | Leu | Met | Asn | Cys | Gly | Gly | Phe | Gly | Met | Glu | Ala | |
| | 375 | | | | | 380 | | | | | 385 | | | | | |

| ACG | CTG | CTG | TTG | GTG | GTC | GGC | TAC | TCG | CAC | TCC | AAG | GGC | GTG | GCC | ATC | 1675 |
| Thr | Leu | Leu | Leu | Val | Val | Gly | Tyr | Ser | His | Ser | Lys | Gly | Val | Ala | Ile | |
| 390 | | | | | 395 | | | | | 400 | | | | | 405 | |

| TCC | TTC | CTG | GTC | CTA | GCC | GTG | GGC | TTC | AGC | GGC | TTC | GCC | ATC | TCT | GGG | 1723 |
| Ser | Phe | Leu | Val | Leu | Ala | Val | Gly | Phe | Ser | Gly | Phe | Ala | Ile | Ser | Gly | |
| | | | | 410 | | | | | 415 | | | | | 420 | | |

| TTC | AAC | GTG | AAC | CAC | CTG | GAC | ATA | GCC | CCG | CGC | TAC | GCC | AGC | ATC | CTC | 1771 |
| Phe | Asn | Val | Asn | His | Leu | Asp | Ile | Ala | Pro | Arg | Tyr | Ala | Ser | Ile | Leu | |
| | | | 425 | | | | | 430 | | | | | 435 | | | |

| ATG | GGC | ATC | TCC | AAC | GGC | GTG | GGC | ACA | CTG | TCG | GGC | ATG | GTG | TGC | CCC | 1819 |
| Met | Gly | Ile | Ser | Asn | Gly | Val | Gly | Thr | Leu | Ser | Gly | Met | Val | Cys | Pro | |
| | | 440 | | | | | 445 | | | | | 450 | | | | |

| ATC | ATC | GTG | GGG | GCC | ATG | ACT | AAG | CAC | AAG | ACT | CGG | GAG | GAG | TGG | CAG | 1867 |
| Ile | Ile | Val | Gly | Ala | Met | Thr | Lys | His | Lys | Thr | Arg | Glu | Glu | Trp | Gln | |
| | 455 | | | | | 460 | | | | | 465 | | | | | |

| TAC | GTG | TTC | CTA | ATT | GCC | TCC | CTG | GTG | CAC | TAT | GGA | GGT | GTC | ATC | TTC | 1915 |
| Tyr | Val | Phe | Leu | Ile | Ala | Ser | Leu | Val | His | Tyr | Gly | Gly | Val | Ile | Phe | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 470 |     |     |     |     | 475 |     |     |     |     | 480 |     |     | 485 |      |
| TAC | GGG | GTC | TTT | GCT | TCT | GGA | GAG | AAG | CAG | CCG | TGG | GCA | GAG | CCT | GAG | 1963 |
| Tyr | Gly | Val | Phe | Ala | Ser | Gly | Glu | Lys | Gln | Pro | Trp | Ala | Glu | Pro | Glu |      |
|     |     | 490 |     |     |     |     | 495 |     |     |     |     |     |     | 500 |     |      |
| GAG | ATG | AGC | GAG | GAG | AAG | TGT | GGC | TTC | GTT | GGC | CAT | GAC | CAG | CTG | GCT | 2011 |
| Glu | Met | Ser | Glu | Glu | Lys | Cys | Gly | Phe | Val | Gly | His | Asp | Gln | Leu | Ala |      |
|     |     |     | 505 |     |     |     |     | 510 |     |     |     |     | 515 |     |     |      |
| GGC | AGT | GAC | GAC | AGC | GAA | ATG | GAG | GAT | GAG | GCT | GAG | CCC | CCG | GGG | GCA | 2059 |
| Gly | Ser | Asp | Asp | Ser | Glu | Met | Glu | Asp | Glu | Ala | Glu | Pro | Pro | Gly | Ala |      |
|     |     | 520 |     |     |     |     | 525 |     |     |     |     | 530 |     |     |     |      |
| CCC | CCT | GCA | CCC | CCG | CCC | TCC | TAT | GGG | GCC | ACA | CAC | AGC | ACA | TTT | CAG | 2107 |
| Pro | Pro | Ala | Pro | Pro | Pro | Ser | Tyr | Gly | Ala | Thr | His | Ser | Thr | Phe | Gln |      |
|     | 535 |     |     |     |     |     | 540 |     |     |     |     | 545 |     |     |     |      |
| CCC | CCC | AGG | CCC | CCA | CCC | CCT | GTC | CGG | GAC | TAC | TGACCATGTG | | CCTCCCACTG | | | 2160 |
| Pro | Pro | Arg | Pro | Pro | Pro | Pro | Val | Arg | Asp | Tyr |     |     |     |     |     |      |
| 550 |     |     |     |     | 555 |     |     |     |     | 560 |     |     |     |     |     |      |

```
AATGGCAGTT  TCCAGGACCT  CCATTCCACT  CATCTCTGGC  CTGAGTGACA  GTGTCAAGGA    2220
ACCCTGCTCC  TCTCTGTCCT  GCCTCAGGCC  TAAGAAGCAC  TCTCCCTTGT  TCCCAGTGCT    2280
GTCAAATCCT  CTTTCCTTCC  CAATTGCCTC  TCAGGGGTAG  TGAAGCTGCA  GACTGACAGT    2340
TTCAAGGATA  CCCAAATTCC  CCTAAAGGTT  CCCTCTCCAC  CCGTTCTGCC  TCAGTGGTTT    2400
CAAATCTCTC  CTTTCAGGGC  TTTATTTGAA  TGGACAGTTC  GACCTCTTAC  TCTCTCTTGT    2460
GGTTTTGAGG  CACCCACACC  CCCCGCTTTC  CTTTATCTCC  AGGGACTCTC  AGGCTAACCT    2520
TTGAGATCAC  TCAGCTCCCA  TCTCCTTTCA  GAAAAATTCA  AGGTCCTCCT  CTAGAAGTTT    2580
CAAATCTCTC  CCAACTCTGT  TCTGCATCTT  CCAGATTGGT  TTAACCAATT  ACTCGTCCCC    2640
GCCATTCCAG  GGATTGATTC  TCACCAGCGT  TTCTGATGGA  AAATGGCGGG  AATTCCTGCA    2700
GCCCGGGGGA  TCCACT                                                        2716
```

( 2 ) INFORMATION FOR SEQ ID NO:2:

( i ) SEQUENCE CHARACTERISTICS:
        ( A ) LENGTH: 560 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Phe  Arg  Gln  Glu  Glu  Phe  Arg  Lys  Leu  Ala  Gly  Arg  Ala  Leu
 1                    5                   10                      15

Gly  Lys  Leu  His  Arg  Leu  Leu  Glu  Lys  Arg  Gln  Glu  Gly  Ala  Glu  Thr
                20                   25                      30

Leu  Glu  Leu  Ser  Ala  Asp  Gly  Arg  Pro  Val  Thr  Thr  Gln  Thr  Arg  Asp
           35                   40                      45

Pro  Pro  Val  Val  Asp  Cys  Thr  Cys  Phe  Gly  Leu  Pro  Arg  Arg  Tyr  Ile
      50                   55                      60

Ile  Ala  Ile  Met  Ser  Gly  Leu  Gly  Phe  Cys  Ile  Ser  Phe  Gly  Ile  Arg
 65                   70                      75                          80

Cys  Asn  Leu  Gly  Val  Ala  Ile  Val  Ser  Met  Val  Asn  Asn  Ser  Thr  Thr
                85                   90                      95

His  Arg  Gly  Gly  His  Val  Val  Val  Gln  Lys  Ala  Gln  Phe  Ser  Trp  Asp
               100                  105                     110

Pro  Glu  Thr  Val  Gly  Leu  Ile  His  Gly  Ser  Phe  Phe  Trp  Gly  Tyr  Ile
           115                  120                     125

Val  Thr  Gln  Ile  Pro  Gly  Gly  Phe  Ile  Cys  Gln  Lys  Phe  Ala  Ala  Asn
          130                  135                     140
```

```
Arg Val Phe Gly Phe Ala Ile Val Ala Thr Ser Thr Leu Asn Met Leu
145                 150                 155                 160

Ile Pro Ser Ala Ala Arg Val His Tyr Gly Cys Val Ile Phe Val Arg
                165                 170                 175

Ile Leu Gln Gly Leu Val Glu Gly Val Thr Tyr Pro Ala Cys His Gly
            180                 185                 190

Ile Trp Ser Lys Trp Ala Pro Pro Leu Glu Arg Ser Arg Leu Ala Thr
        195                 200                 205

Thr Ala Phe Cys Gly Ser Tyr Ala Gly Ala Val Val Ala Met Pro Leu
    210                 215                 220

Ala Gly Val Leu Val Gln Tyr Ser Gly Trp Ser Ser Val Phe Tyr Val
225                 230                 235                 240

Tyr Gly Ser Phe Gly Ile Phe Trp Tyr Leu Phe Trp Leu Leu Val Ser
                245                 250                 255

Tyr Glu Ser Pro Ala Leu His Pro Ser Ile Ser Glu Glu Glu Arg Lys
            260                 265                 270

Tyr Ile Glu Asp Ala Ile Gly Glu Ser Ala Lys Leu Met Asn Pro Leu
        275                 280                 285

Thr Lys Phe Ser Thr Pro Trp Arg Arg Phe Phe Thr Ser Met Pro Val
    290                 295                 300

Tyr Ala Ile Ile Val Ala Asn Phe Cys Arg Ser Trp Thr Phe Tyr Leu
305                 310                 315                 320

Leu Leu Ile Ser Gln Pro Asp Tyr Phe Glu Glu Val Phe Gly Phe Glu
                325                 330                 335

Ile Ser Lys Val Gly Leu Val Ser Ala Leu Pro His Leu Val Met Thr
            340                 345                 350

Ile Ile Val Pro Ile Gly Gly Gln Ile Ala Asp Phe Leu Arg Ser Arg
        355                 360                 365

Arg Ile Met Ser Thr Thr Asn Val Arg Lys Leu Met Asn Cys Gly Gly
    370                 375                 380

Phe Gly Met Glu Ala Thr Leu Leu Leu Val Val Gly Tyr Ser His Ser
385                 390                 395                 400

Lys Gly Val Ala Ile Ser Phe Leu Val Leu Ala Val Gly Phe Ser Gly
                405                 410                 415

Phe Ala Ile Ser Gly Phe Asn Val Asn His Leu Asp Ile Ala Pro Arg
            420                 425                 430

Tyr Ala Ser Ile Leu Met Gly Ile Ser Asn Gly Val Gly Thr Leu Ser
        435                 440                 445

Gly Met Val Cys Pro Ile Ile Val Gly Ala Met Thr Lys His Lys Thr
    450                 455                 460

Arg Glu Glu Trp Gln Tyr Val Phe Leu Ile Ala Ser Leu Val His Tyr
465                 470                 475                 480

Gly Gly Val Ile Phe Tyr Gly Val Phe Ala Ser Gly Glu Lys Gln Pro
                485                 490                 495

Trp Ala Glu Pro Glu Glu Met Ser Glu Glu Lys Cys Gly Phe Val Gly
            500                 505                 510

His Asp Gln Leu Ala Gly Ser Asp Asp Ser Glu Met Glu Asp Glu Ala
        515                 520                 525

Glu Pro Pro Gly Ala Pro Pro Ala Pro Pro Pro Ser Tyr Gly Ala Thr
    530                 535                 540

His Ser Thr Phe Gln Pro Pro Arg Pro Pro Pro Pro Val Arg Asp Tyr
545                 550                 555                 560
```

5,618,918

( 2 ) INFORMATION FOR SEQ ID NO:3:

( i ) SEQUENCE CHARACTERISTICS:
        ( A ) LENGTH: 2716 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

| | | | | | | |
|---|---|---|---|---|---|---|
| CGAUAAGCUU | GAUAUCGAAU | UCCGGACUCU | UGCUCGGGCG | CCUUAACCCG | GCGUUCGGUU | 60 |
| CAUCCCGCAG | CGCCAGUUCU | GCUUACCAAA | AGUGGCCCAC | UAGGCACUCG | CAUUCCACGC | 120 |
| CCGGCUCCAC | GCCAGCGAGC | CGGGCUUCUU | ACCCAUUUAA | AGUUUGAGAA | UAGGUUGAGA | 180 |
| UCGUUUCGGC | CCCAAGACCU | CUAAUCAUUC | GCUUUACCGG | AUAAAACUGC | GUGGCGGGGG | 240 |
| UGCGUCGGGU | CUGCGAGAGC | GCCAGCUAUC | CUGAGGGAAA | CUUCGGAGGG | AACCAGCUAC | 300 |
| UAGAUGGUUC | GAUUAGUCUU | UCGCCCCUAU | ACCCAGGUCG | GACGACCGAU | UUGCACGUCA | 360 |
| GGACCGCUAC | GGACCUCCAC | CAGAGUUUCC | UCUGGCUUCG | CCCUGCCCAG | GCGAUCGGCG | 420 |
| GGGGGACCC | GCGGGUGAC | CGGCGGCAGG | AGCCGCCACC | AUGGAGUUCC | GCCAGGAGGA | 480 |
| GUUUCGGAAG | CUAGCGGGUC | GUGCUCUCGG | GAAGCUGCAC | CGCCUUCUGG | AGAAGCGGCA | 540 |
| GGAAGGCGCG | GAGACGCUGG | AGCUGAGUGC | GGAUGGGCGC | CCGGUGACCA | CGCAGACCCG | 600 |
| GGACCCGCCG | GUGGUGGACU | GCACCUGCUU | CGGCCUCCCU | CGCCGCUACA | UUAUCGCCAU | 660 |
| CAUGAGUGGU | CUGGGCUUCU | GCAUCAGCUU | UGGCAUCCGC | UGCAACCUGG | GCGUGGCCAU | 720 |
| CGUCUCCAUG | GUCAAUAACA | GCACGACCCA | CCGCGGGGGC | CACGUGGUGG | UGCAGAAAGC | 780 |
| CCAGUUCAGC | UGGGAUCCAG | AGACUGUCGG | CCUCAUACAC | GGCUCCUUUU | UCUGGGGCUA | 840 |
| CAUUGUCACU | CAGAUUCCAG | GAGGAUUUAU | CUGUCAAAAA | UUUGCAGCCA | ACAGAGUUUU | 900 |
| CGGCUUUGCU | AUUGUGGCAA | CAUCCACUCU | AAACAUGCUG | AUCCCUCAG | CUGCCCGCGU | 960 |
| CCACUAUGGC | UGUGUCAUCU | UCGUGAGGAU | CCUGCAGGGG | UUGGUAGAGG | GGGUCACAUA | 1020 |
| CCCCGCCUGC | CAUGGGAUCU | GGAGCAAAUG | GGCCCCACCC | UUAGAACGGA | GUCGCCUGGC | 1080 |
| GACGACAGCC | UUUUGUGGUU | CCUAUGCUGG | GGCGGUGGUC | GCGAUGCCCC | UCGCCGGGGU | 1140 |
| CCUUGUGCAG | UACUCAGGAU | GGAGCUCUGU | UUUCUACGUC | UACGGCAGCU | UCGGGAUCUU | 1200 |
| CUGGUACCUG | UUCUGGCUGC | UCGUCUCCUA | CGAGUCCCCC | GCGCUGCACC | CCAGCAUCUC | 1260 |
| GGAGGAGGAG | CGCAAGUACA | UCGAGGACGC | CAUCGGAGAG | AGCGCGAAAC | UCAUGAACCC | 1320 |
| CCUCACGAAG | UUUAGCACUC | CCUGGCGGCG | CUUCUUCACG | UCUAUGCCAG | UCUAUGCCAU | 1380 |
| CAUCGUGGCC | AACUUCUGCC | GCAGCUGGAC | GUUCUACCUG | CUGCUCAUCU | CCCAGCCCGA | 1440 |
| CUACUUCGAA | GAAGUGUUCG | GCUUCGAGAU | CAGCAAGGUA | GGCCUGGUGU | CCGCGCUGCC | 1500 |
| CCACCUGGUC | AUGACCAUCA | UCGUGCCCAU | CGGCGGCCAG | AUCGCGGACU | UCCUGCGGAG | 1560 |
| CCGCCGCAUC | AUGUCCACCA | CCAACGUGCG | CAAGUUGAUG | AACUGCGGAG | GCUUCGGCAU | 1620 |
| GGAAGCCACG | CUGCUGUUGG | UGGUCGGCUA | CUCGCACUCC | AAGGGCGUGG | CCAUCUCCUU | 1680 |
| CCUGGUCCUA | GCCGUGGGCU | UCAGCGGCUU | CGCCAUCUCU | GGGUUCAACG | UGAACCACCU | 1740 |
| GGACAUAGCC | CCGCGCUACG | CCAGCAUCCU | CAUGGGCAUC | UCCAACGGCG | UGGGCACACU | 1800 |
| GUCGGGCAUG | GUGUGCCCCA | UCAUCGUGGG | GGCCAUGACU | AAGCACAAGA | CUCGGGAGGA | 1860 |
| GUGGCAGUAC | GUGUUCCUAA | UUGCCUCCCU | GGUGCACUAU | GGAGGUGUCA | UCUUCUACGG | 1920 |
| GGUCUUUGCU | UCUGGAGAGA | AGCAGCCGUG | GGCAGAGCCU | GAGGAGAUGA | GCGAGGAGAA | 1980 |
| GUGUGGCUUC | GUUGGCCAUG | ACCAGCUGGC | UGGCAGUGAC | GACAGCGAAA | UGGAGGAUGA | 2040 |

| | | | | | | |
|---|---|---|---|---|---|---|
| GGCUGAGCCC | CCGGGGGCAC | CCCCUGCACC | CCCGCCCUCC | UAUGGGGCCA | CACACAGCAC | 2100 |
| AUUUCAGCCC | CCCAGGCCCC | CACCCCCUGU | CCGGGACUAC | UGACCAUGUG | CCUCCCACUG | 2160 |
| AAUGGCAGUU | UCCAGGACCU | CCAUUCCACU | CAUCUCUGGC | CUGAGUGACA | GUGUCAAGGA | 2220 |
| ACCCUGCUCC | UCUCUGUCCU | GCCUCAGGCC | UAAGAAGCAC | UCUCCCUUGU | UCCCAGUGCU | 2280 |
| GUCAAAUCCU | CUUUCCUUCC | CAAUUGCCUC | UCAGGGGUAG | UGAAGCUGCA | GACUGACAGU | 2340 |
| UUCAAGGAUA | CCCAAAUUCC | CCUAAAGGUU | CCCUCUCCAC | CCGUUCUGCC | UCAGUGGUUU | 2400 |
| CAAAUCUCUC | CUUUCAGGGC | UUUAUUUGAA | UGGACAGUUC | GACCUCUUAC | UCUCUCUUGU | 2460 |
| GGUUUUGAGG | CACCCACACC | CCCCGCUUUC | CUUUAUCUCC | AGGGACUCUC | AGGCUAACCU | 2520 |
| UUGAGAUCAC | UCAGCUCCCA | UCUCCUUUCA | GAAAAAUUCA | AGGUCCUCCU | CUAGAAGUUU | 2580 |
| CAAAUCUCUC | CCAACUCUGU | UCUGCAUCUU | CCAGAUUGGU | UUAACCAAUU | ACUCGUCCCC | 2640 |
| GCCAUUCCAG | GGAUUGAUUC | UCACCAGCGU | UUCUGAUGGA | AAAUGGCGGG | AAUUCCUGCA | 2700 |
| GCCCGGGGGA | UCCACU | | | | | 2716 |